United States Patent
Zhang et al.

(10) Patent No.: US 10,221,185 B2
(45) Date of Patent: Mar. 5, 2019

(54) CRYSTAL FORM OF SUBSTITUTED AMINOPYRAN DERIVATIVEK

(71) Applicant: Sichuan Haisco Pharmaceutical Co., Ltd., Chengdu, Sichuan (CN)

(72) Inventors: Chen Zhang, Chengdu (CN); Jianmin Wang, Chengdu (CN)

(73) Assignee: Sichuan Haisco Pharmaceutical Co., Ltd., Sichuan (CN)

( * ) Notice: Subject to any disclaimer, the term of this patent is extended or adjusted under 35 U.S.C. 154(b) by 0 days.

(21) Appl. No.: 16/065,544

(22) PCT Filed: Dec. 12, 2016

(86) PCT No.: PCT/CN2016/109388
§ 371 (c)(1),
(2) Date: Jun. 22, 2018

(87) PCT Pub. No.: WO2017/107791
PCT Pub. Date: Jun. 29, 2017

(65) Prior Publication Data
US 2018/0370980 A1    Dec. 27, 2018

(30) Foreign Application Priority Data
Dec. 25, 2015  (CN) .......................... 2015 1 0999152

(51) Int. Cl.
*C07D 487/04*    (2006.01)
*A61K 31/4162*   (2006.01)
*A61P 3/10*      (2006.01)

(52) U.S. Cl.
CPC .............. *C07D 487/04* (2013.01); *A61P 3/10* (2018.01); *C07B 2200/13* (2013.01)

(58) Field of Classification Search
None
See application file for complete search history.

(56) References Cited

U.S. PATENT DOCUMENTS 8,143,289 B2 *  3/2012  Biftu .................... C07D 487/04
                                                514/338
2017/0121338 A1   5/2017  Zhang et al.

OTHER PUBLICATIONS

Abstract of WO 2015/192701 A1 (Sichuan Haisco Pharma. Co., Ltd.).
International Search Report regarding PCT Application No. PCT/CN2016/109388, dated Mar. 16, 2017, 3 pps.

* cited by examiner

*Primary Examiner* — Kamal A Saeed
(74) *Attorney, Agent, or Firm* — Foley & Lardner LLP

(57) ABSTRACT

The present invention relates to a crystal form of a substituted aminopyran compound, and a pharmaceutical composition, a preparation method and a use thereof in the preparation of a drug for treating type II diabetes. In particular, the present invention relates to a crystal form IV of a compound as shown by formula (I) and a pharmaceutical composition, a preparation method and a use thereof in the preparation of a drug for treating type II diabetes.

18 Claims, 7 Drawing Sheets

CRYSTAL FORM OF SUBSTITUTED AMINOPYRAN DERIVATIVEK

CROSS-REFERENCE TO RELATED APPLICATIONS

This application is a U.S. national stage of international patent application PCT/CN2016/109388, filed on Dec. 12, 2016, which claims priority to Chinese application CN 201510999152.1, filed on Dec. 25, 2015.

TECHNICAL FIELD

The present invention relates to a crystal form of a substituted aminopyran derivative or a hydrate or solvate thereof, a method for the preparation of the same, a pharmaceutical composition comprising the same, and the use thereof in the manufacture of a di-peptidyl peptidase IV (DPP-IV) inhibitor.

BACKGROUND ART

Di-peptidyl peptidase IV (DPP-IV, EC3.4.14.5) is a serine protease which hydrolytically cleaves an N-terminal dipeptide from the N-terminus of an L-proline- or L-alanine-containing polypeptide. DPP-IV inhibitors exert their functions by enhancing the activity of incretins, and are non-insulin therapeutic drugs. DPP-IV inhibitors do not cause adverse effects such as body-weight gain and edema.

Patent application PCT/CN2015/078923 discloses a novel pyran derivative (2R,3S,5R,6S)-2-(2,5-difluorophenyl)-5-(2-(methylsulfonyl)-pyrrolo[3,4]pyrazol-5(2H,4H,6H)-yl)-6-(trifluoromethyl)tetrahydro-2H-pyran-3-amine as represented by structural formula (I) below, referred to as Compound A herein. This structure shows good inhibition on DPP-IV, and has a potential of preventing and/or treating type II diabetes.

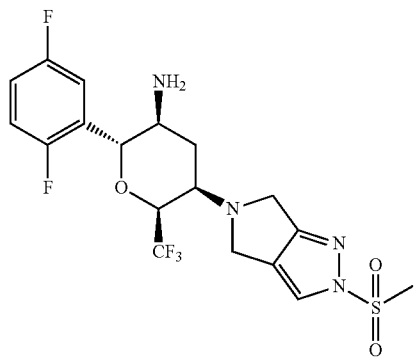

(I)

SUMMARY OF INVENTION

An embodiment of the present invention provides Crystal form IV of Compound A (2R,3S,5R,6S)-2-(2,5-difluorophenyl)-5-(2-(methylsulfonyl)-pyrrolo[3,4]pyrazol-5(2H,4H,6H)-yl)-6-(trifluoromethyl)tetrahydro-2H-pyran-3-amine, wherein Compound A is represented by structural formula (I) below:

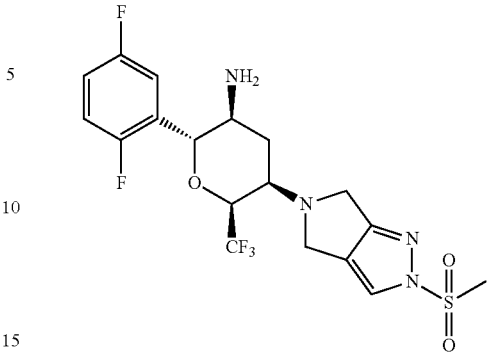

(I)

Crystal form IV according to the present invention has advantages such as easy processing and crystallization, easy handling, good stability, high bioavailability, good pressure stability, and easy administration, making it particularly suitable for manufacture of various dosage forms.

Crystal form IV according to the present invention exhibits pharmaceutical advantages over the amorphous free base of Compound A. In particular, the crystal form enhances chemical and physical stability, and is more suitable for the manufacture of solid dosage forms comprising the pharmacologically active ingredient.

The crystal form according to the present invention is present in an amount of about 5% to about 100% by weight of the active pharmaceutical ingredient. In certain embodiments, the crystal form according to the present invention is present in an amount of about 10% to about 100% by weight of the active pharmaceutical ingredient. In certain embodiments, the crystal form according to the present invention is present in an amount of about 15% to about 100% by weight of the active pharmaceutical ingredient. In certain embodiments, the crystal form according to the present invention is present in an amount of about 20% to about 100% by weight of the active pharmaceutical ingredient. In certain embodiments, the crystal form according to the present invention is present in an amount of about 25% to about 100% by weight of the active pharmaceutical ingredient. In certain embodiments, the crystal form according to the present invention is present in an amount of about 30% to about 100% by weight of the active pharmaceutical ingredient. In certain embodiments, the crystal form according to the present invention is present in an amount of about 35% to about 100% by weight of the active pharmaceutical ingredient. In certain embodiments, the crystal form according to the present invention is present in an amount of about 40% to about 100% by weight of the active pharmaceutical ingredient. In certain embodiments, the crystal form according to the present invention is present in an amount of about 45% to about 100% by weight of the active pharmaceutical ingredient. In certain embodiments, the crystal form according to the present invention is present in an amount of about 50% to about 100% by weight of the active pharmaceutical ingredient. In certain embodiments, the crystal form according to the present invention is present in an amount of about 55% to about 100% by weight of the active pharmaceutical ingredient. In certain embodiments, the crystal form according to the present invention is present in an amount of about 60% to about 100% by weight of the active pharmaceutical ingredient. In certain embodiments, the crystal form according to the present invention is present in an amount of about 65% to about 100% by weight of the active pharmaceutical ingredient. In certain embodiments, the crystal form according to the present invention is present in an amount of about 70% to about 100% by weight of the active pharmaceutical ingredient. In certain embodiments, the crystal form according to the present invention is present in an amount of about 75% to about 100% by weight of the active pharmaceutical ingredient. In certain embodiments, the crystal form according to the present invention is present in an amount of about 80% to about 100% by weight of the active pharmaceutical ingredient. In certain embodiments, the crystal form according to the present invention is present in an amount of about 85% to about 100% by weight of the active pharmaceutical ingredient. In certain embodiments, the crystal form according to the present invention is present in an amount of about 90% to about 100% by weight of the active pharmaceutical ingredient. In certain embodiments, the crystal form according to the present invention is present in an amount of about 95% to about 100% by weight of the active pharmaceutical ingredient. In certain embodiments, the crystal form according to the present invention is present in an amount of about 98% to about 100% by weight of the active pharmaceutical ingredient. In certain embodiments, the crystal form according to the present invention is present in an amount of about 99% to about 100% by weight of the active pharmaceutical ingredient. In certain embodiments, nearly all of the active pharmaceutical ingredient is the crystal form according to the present invention, that is, the active pharmaceutical ingredient is substantially phase-pure crystal.

Unless particularly specified, Compound A in the context of the present invention refers to the amorphous form of Compound A.

In an embodiment of the present invention, the X-ray powder diffraction pattern of anhydrous Compound A (crystal form IV) measured using Cu—Kα radiation contains characteristic diffraction peaks present at 2θ positions of 9.2°±0.2°, 12.8°±0.2°, 16.2°±0.2°, 18.4°±0.2°, 20.5°±0.2° and 26.5°±0.2°.

In an embodiment, the X-ray powder diffraction pattern of Crystal form IV contains additional characteristic diffraction peaks present at 2θ positions of 11.9°±0.2°, 12.3°±0.2°, 15.2°±0.2°, 16.6°±0.2°, 18.7°±0.2° and 24.9°±0.2°.

In another embodiment, the X-ray powder diffraction pattern of Crystal form IV contains additional characteristic diffraction peaks present at 2θ positions of 20.1°±0.2°, 20.7°±0.2°, 21.4°±0.2°, 22.3°±0.2°, 23.2°±0.2° and 24.6°±0.2°.

In yet another embodiment, the X-ray powder diffraction pattern of Crystal form IV contains additional characteristic diffraction peaks present at 2θ positions of 3.6°±0.2°, 9.9°±0.2°, 21.7°±0.2°, 24.1°±0.2°, 26.0°±0.2°, 28.3°±0.2°, 30.7°±0.2° and 34.1°±0.2°.

In a further embodiment, the X-ray powder diffraction pattern of Crystal form IV is substantially as shown in FIG. 10.

In an embodiment, the Differential Scanning calorimeter (DSC) curve of Crystal form IV according to the present invention shows an endothermic curve wherein Tinitial=155.82° C., Tpeak=158.57° C., and ΔH=64.44 J/g.

In an embodiment, the Differential Scanning calorimeter (DSC) curve of Crystal form IV according to the present invention is as shown in FIG. 11.

In an embodiment, the Thermogravimetric Analysis (TGA) curve of Crystal form IV according to the present invention shows a mass loss of 1.0% before 150° C. and a decomposition temperature of 222.1° C.

In an embodiment, the Thermogravimetric Analysis curve of Crystal form IV according to the present invention is as shown in FIG. 12.

It is to be understood that, as well known in the field of Differential Scanning calorimeter (DSC), the height of melting peak in a DSC curve depends on many factors related to sample preparation and the geometric shape of apparatus, while the position of peak is relatively insensitive to experimental details. Therefore, in some embodiments, the DSC curve of the crystalline compound according to the present invention showing characteristic peak positions has essentially the same nature as the DSC curve provided in the figures of this disclosure, with an error margin of ±3° C.

An embodiment of the present invention further relates to a pharmaceutical composition comprising a therapeutically effective amount of the crystal form of the compound according to the present invention, and one or more pharmaceutically acceptable carriers or excipients.

The crystal form according to the present invention as an active pharmaceutical ingredient, or a pharmaceutical composition containing the crystal form as an active pharmaceutical ingredient, may be used to manufacture a medicament for preventing and/or treating diabetes, diabetic retinopathy, diabetic neuropathy, or diabetic nephropathy, preferably type II diabetes.

An embodiment of the present invention discloses a method for treating metabolic diseases, comprising administering one or more crystal forms of Compound A according to the present invention or a pharmaceutical composition comprising the crystal forms according to the present invention.

The scope of the present invention also includes those having essentially the same pattern or curve as the X-ray powder diffraction pattern, DSC curves, or TGA curves disclosed herein.

An embodiment of the present invention provides a method for preparing Crystal form IV of the compound of formula (I), comprising subjecting the amorphous form of the compound of formula (I) or any crystal form of the compound of formula (I) to recrystallization or slurrying, wherein the solvent for the recrystallization or slurrying is selected from one of, or a mixed solvent of two or more of, ester solvents, ether solvents, alkane solvents, alcohol solvents, and water, preferably a mixture of an ester solvent and an alkane solvent.

In an embodiment of the method for preparing Crystal form IV of the compound of formula (I) according to the present invention, the solvent for the recrystallization or slurrying is selected from one of, or a mixed solvent of two or more of, ethyl acetate, isopropyl ether, methyl t-butyl ether, n-heptane, methanol, ethanol, and water.

In an embodiment of the method for preparing Crystal form IV of the compound of formula (I) according to the present invention, the temperature for the recrystallization or slurrying is 10° C. to 80° C., preferably 10° C. to 50° C., more preferably 20° C. to 40° C.

In an embodiment of the method for preparing Crystal form IV of the compound of formula (I) according to the present invention, the solvent for the recrystallization or slurrying is a mixed solvent of ethyl acetate and n-heptane in a volume ratio of preferably 1:1 to 1:3, more preferably 1:2.

In an embodiment of the method for preparing Crystal form IV of the compound of formula (I) according to the present invention, for crystallization, seeds of Crystal form IV of the compound of formula (I) may optionally be added, followed by conventional posttreatment (e.g. stirring, filtration, etc.), to obtain Crystal form IV of the compound of formula (I).

In an embodiment of the method for preparing Crystal form IV of the compound of formula (I) according to the present invention, the amorphous form of the compound of formula (I) or any crystal form of the compound of formula (I) is treated at a temperature of 100° C. or higher, preferably 140° C.

Unless otherwise indicated, the terms used throughout the specification and claims have the following meanings.

An "effective amount" means an amount of compound that causes a physiological or medical response in a tissue, system or subject and is a desirable amount, including the amount of compound that is, after administered to a subject to be treated, sufficient to prevent occurrence of one or more symptoms of the disease or disorder to be treated or to reduce the symptom(s) to a certain degree.

"IC50" means half maximal inhibitory concentration, the concentration that achieves half of the maximum inhibitory effect.

The structure of the crystal form according to the present invention may be analyzed by various analytical techniques known to a person ordinarily skilled in the art, including but not limited to X-ray powder diffraction (XRD), Differential Scanning calorimeter (DSC), and/or Thermogravimetric Analysis (TGA) (also called Thermogravimetry (TG)).

The X-ray powder diffraction (XRD) instrument used for the present invention was Bruker D8 Advance diffractometer, equipped with a Cu target for Kα radiation (40 Kv, 40 mA) at a wavelength of 1.54 nm, a θ-2θ goniometer, a Mo monochromator, and a Lynxeye detector, using Al2O3 as a calibrating substance, Diffrac Plus XRD Commander as the collecting software, and MDI Jade 6 as the analyzing software; process parameters: specification of the reflexless sample plate: 24.6 mm diameter×1.0 mm thickness, manufactured by MTI corporation; multi-temperature heating station, manufactured by Shanghai Weitu Instrument Technology Ltd., using a copper plate as the sample plate; Detection angle: 3° to 40° 2θ; Step length: 0.02° 2θ.

The Differential Scanning calorimeter (DSC) used for the present invention was TA Instruments Q200 DSC, operated under N2 protection with a gas flow rate of 40 ml/min.

The Thermogravimetric Analysis (TGA) instrument used for the present invention was TA Instruments Q500 TGA, operated under N2 protection with a gas flow rate of 40 ml/min.

It is to be understood that all numerical values described and claimed in accordance with the present invention are all approximate values, and variations in values may be due to calibration of instrument, errors of instrument, purity of crystal, the size of crystal, the size of sample, etc.

It is to be understood that the crystal form according to the present invention is not limited to those represented by patterns or curves completely identical to those shown in the Figures of the present application, such as the XRD, DSC and TGA, and any crystal form having a characteristic pattern or curve substantially or essentially the same as those described in the Figures is within the scope of the present invention.

The crystal form according to the present invention can be prepared by the following conventional methods for preparation of crystal forms:
1) the volatilization method, in which a clear solution of a sample is left open to an atmosphere and volatilized to dry the solvent away at various temperatures;
2) the crystal slurry method, in which an oversaturated solution of a sample (containing undissolved solid) is stirred at a certain temperature in a different solvent system;
3) the anti-solvent method, in which a sample is dissolved in a good solvent and then an anti-solvent is added thereto to precipitate solid, followed by brief stirring and immediate filtration;
4) crystallization by cooling, in which a certain amount of sample is dissolved in a corresponding solvent at a high temperature, directly followed by stirring at room temperature or a low temperature to precipitate crystal;
5) the polymer template method, in which different types of polymer materials are added to a clear solution of a sample, which is left open at room temperature and volatilized to dry the solvent away;
6) the thermal method, in which a sample is treated under a thermal crystallization condition and cooled to room temperature;
7) water vapor diffusion, in which a sample is placed at room temperature in an environment having certain humidity.

After studying the embodiments of the present invention in the specification and examples, it would be apparent for a person skilled in the art to make various modifications and improvements to the present invention without departing from the scope and spirit of the present invention.

DETAILED DESCRIPTION OF INVENTION

Hereinafter the technical solutions of the present invention will be described in details in conjunction with the drawings and examples. However, the scope of the present invention is not limited thereto.

In the Examples, unless particularly specified, solutions refer to aqueous solutions.

Unless particularly specified, crystallization in the experiments is generally carried out at room temperature (20° C. to 30° C., 30% to 70% RH), and the ratio between solvents refers to a ratio by volume.

EXAMPLE 1

Preparation of Compound A

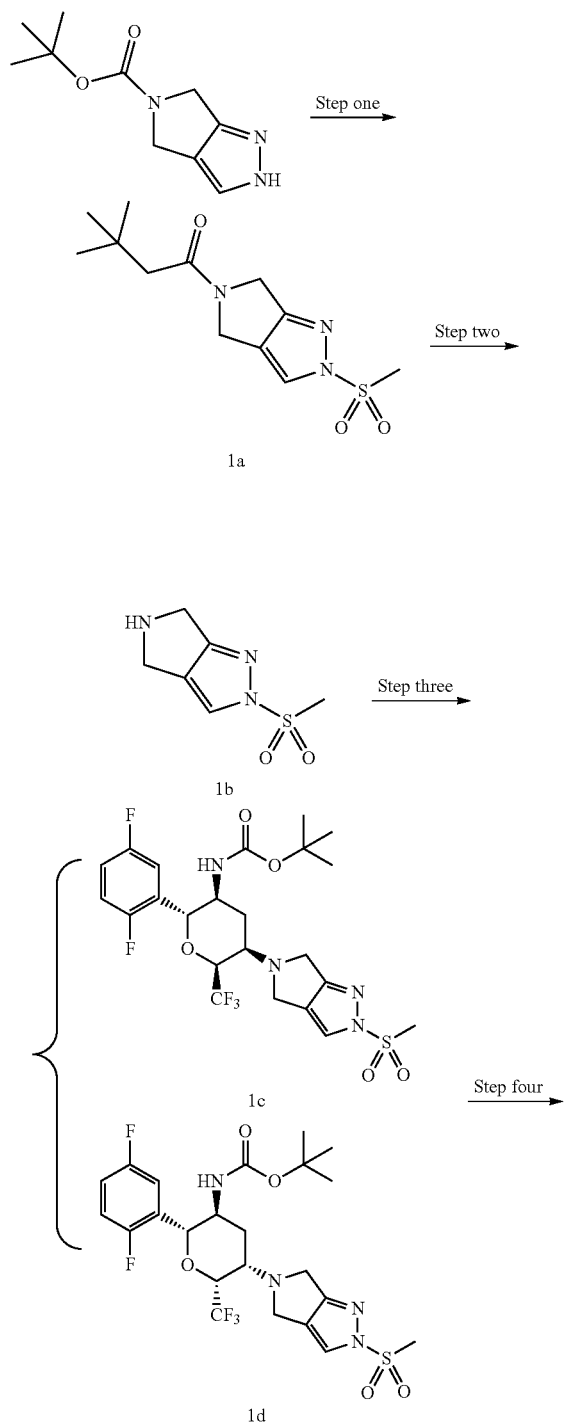

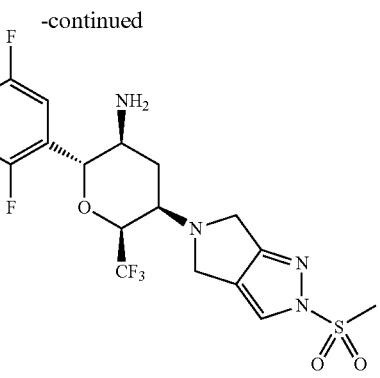

Compound A

For Steps 1-3, see the preparation procedures in WO2015/192701.

Step 4:

(2R,3S,5R,6S)-2-(2,5-difluorophenyl)-5-(2-(methylsulfonyl)pyrrolo[3,4-c]pyrazol-5(2H,4H,6H)-yl)-6-(trifluoromethyl)tetrahydro-2H-pyran-3-amine (Compound A)

Figure 1:
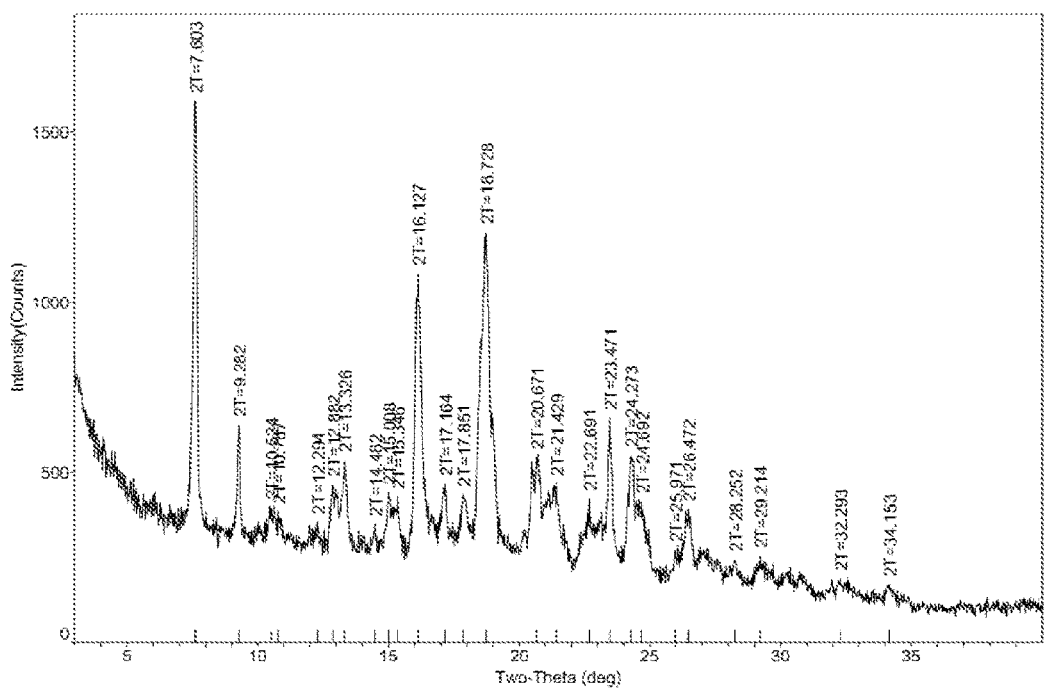
FIG. 1 is an X-ray powder diffraction pattern of Crystal form I of Compound A, obtained using Cu—Kα radiation.
Figure 2:
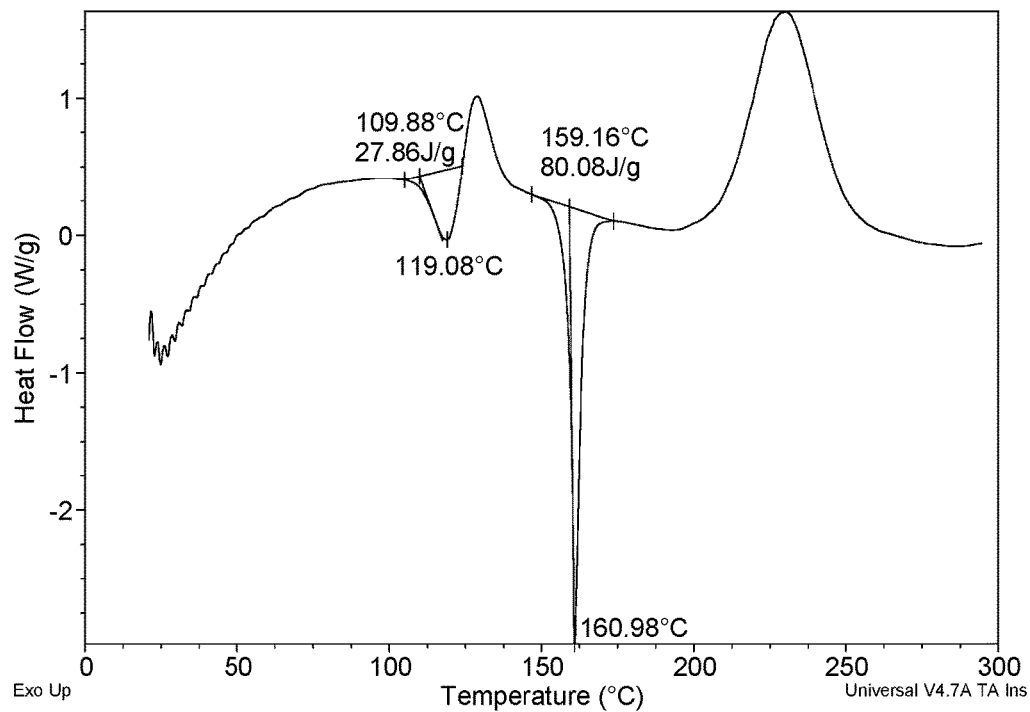
FIG. 2 is a Differential Scanning calorimeter (DSC) curve of Crystal form I of Compound A.
Figure 3:
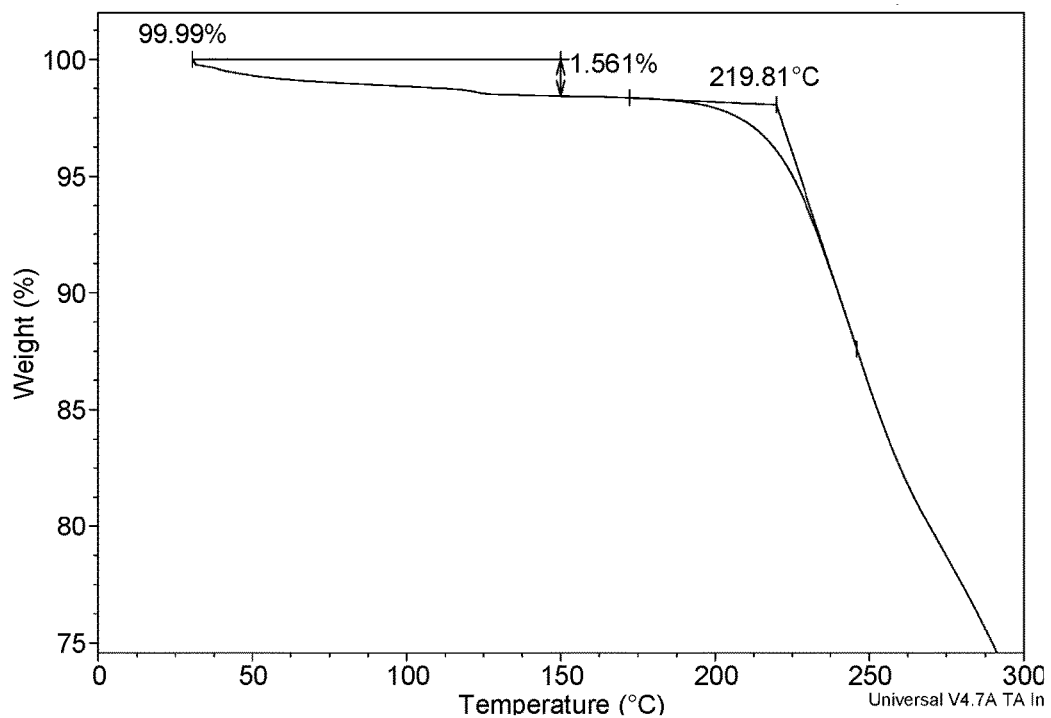
FIG. 3 is a Thermogravimetric Analysis (TGA) curve of Crystal form I of Compound A.

Under a $N_2$ atmosphere at 0° C., Compound 1c (57.5 g, 101.6 mmol) was dissolved in dichloromethane (345 ml) and trifluoroacetic acid (86 ml), followed by stirring at room temperature for 4 hours. After the reaction was complete, the reaction solution was concentrated under reduced pressure and a temperature below 20° C. until it became viscous. Water (600 ml) and dichloromethane (80 ml) were added to the reaction solution, which was stirred and left to be partitioned. Dichloromethane (300 ml) was added to the aqueous phase, which was adjusted to a pH of 9-10 with aqueous ammonia under stirring to be partitioned. The aqueous phase was extracted with dichloromethane (300 ml×2). The organic phases were combined, washed with water (300 ml), dried over anhydrous sodium sulfate, and concentrated. The concentrate was purified by silica gel column chromatography (ethyl acetate/methanol (v/v)=50:1) and dried by rotary evaporation, to obtain Compound A as a white powdery solid (37.8 g, yield 80%). XRD, DSC and TGA analyses showed that it was Crystal form I of Compound A, as shown in FIGS. 1-3.

EXAMPLE 2

Preparation of Crystal Form II of Compound A

Figure 4:
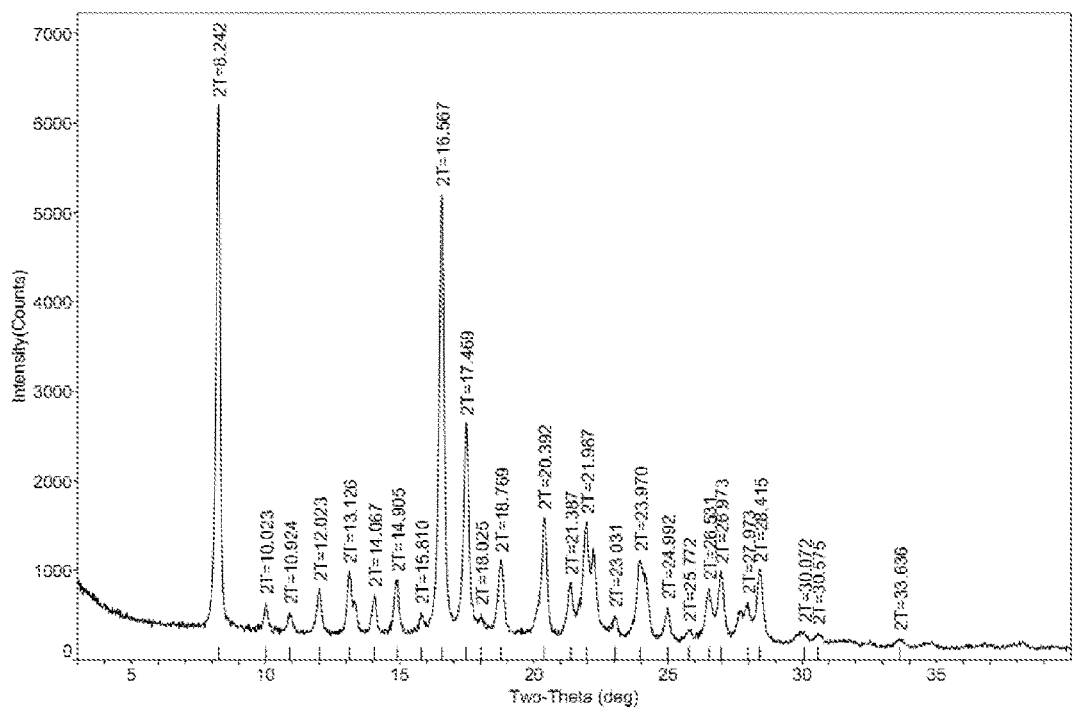
FIG. 4 is an X-ray powder diffraction pattern of Crystal form II of Compound A, obtained using Cu—Kα radiation.
Figure 5:
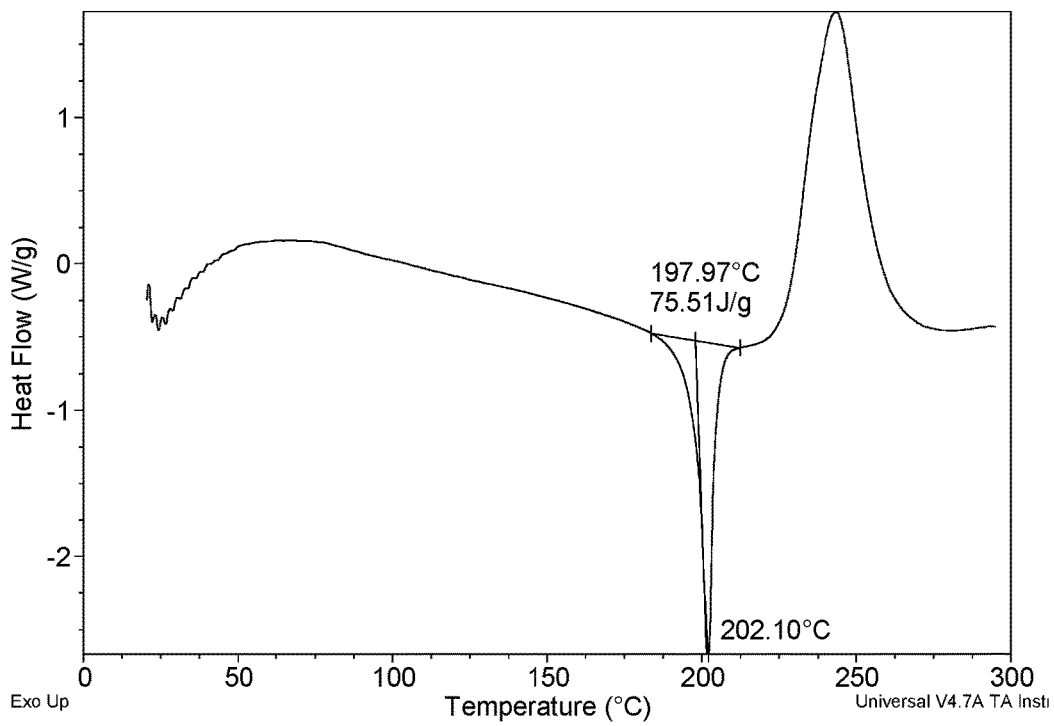
FIG. 5 is a Differential Scanning calorimeter (DSC) curve of Crystal form II of Compound A.
Figure 6:
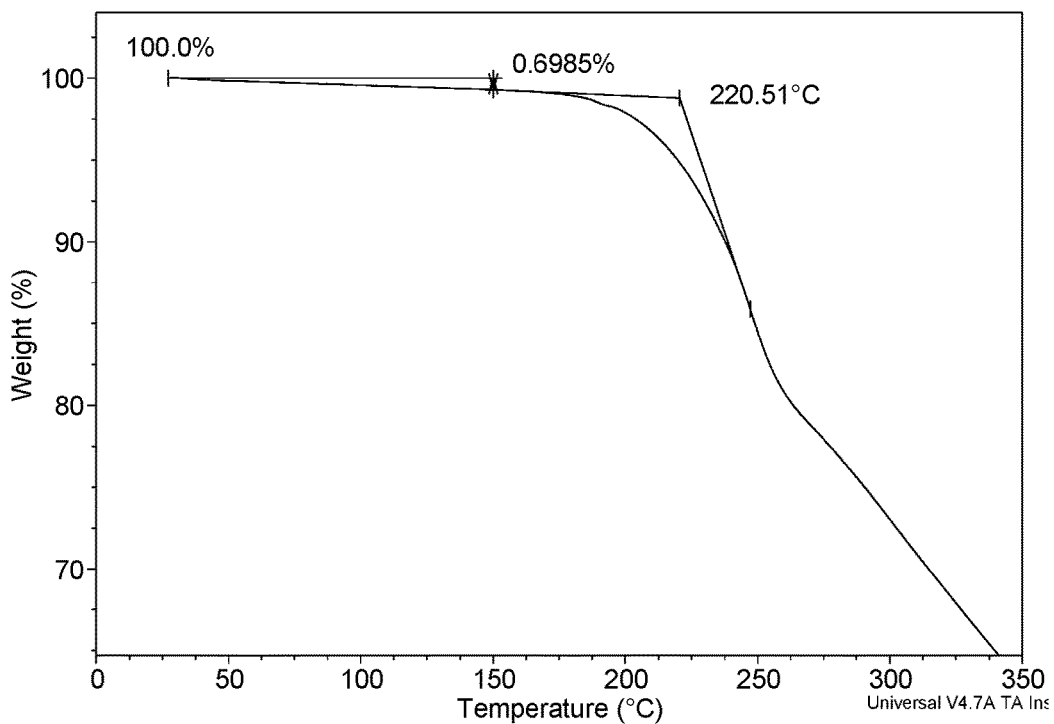
FIG. 6 is a Thermogravimetric Analysis (TGA) curve of Crystal form II of Compound A.

Method 1: At 50° C., Crystal form I of Compound A (50 mg) was dissolved in water (5.0 ml) and acetone (2.8 ml), followed by hot filtration. The filtrate was stirred for 2 days at 3° C., and filtered. The filter cake was vacuum-dried at room temperature to obtain Crystal form II of Compound A, which was characterized by XRD, DSC and TGA as shown in FIGS. 4-6.

EXAMPLE 3

Preparation of Crystal Form III of Compound A

Figure 7:
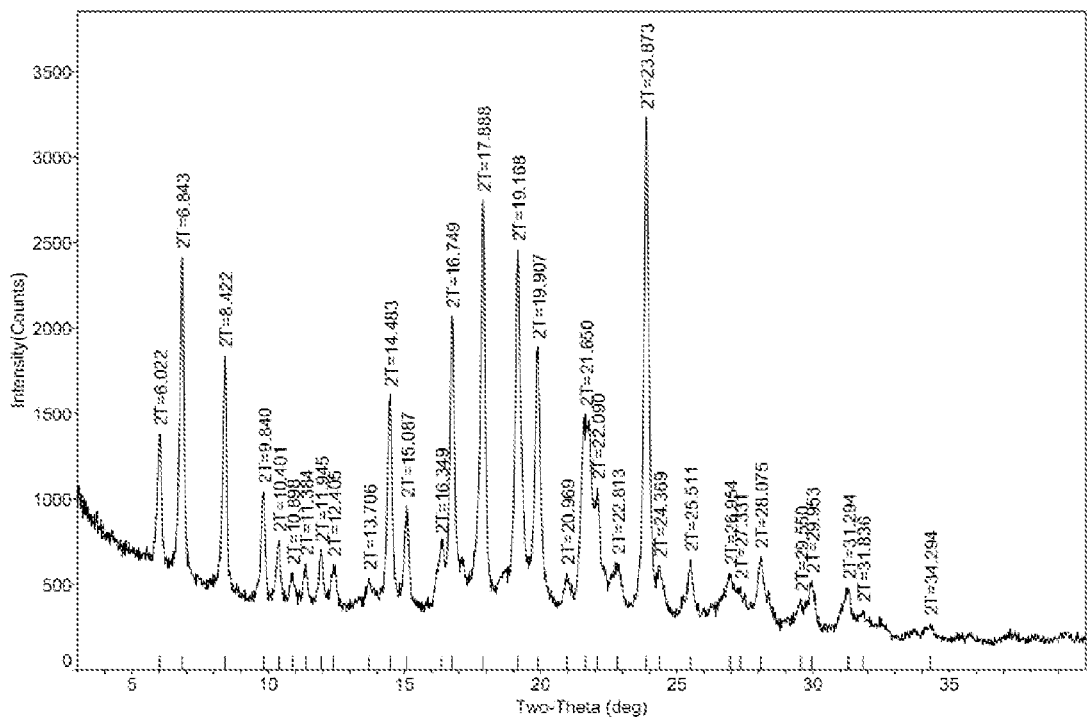
FIG. 7 is an X-ray powder diffraction pattern of Crystal form III of Compound A, obtained using Cu—Kα radiation.
Figure 8:
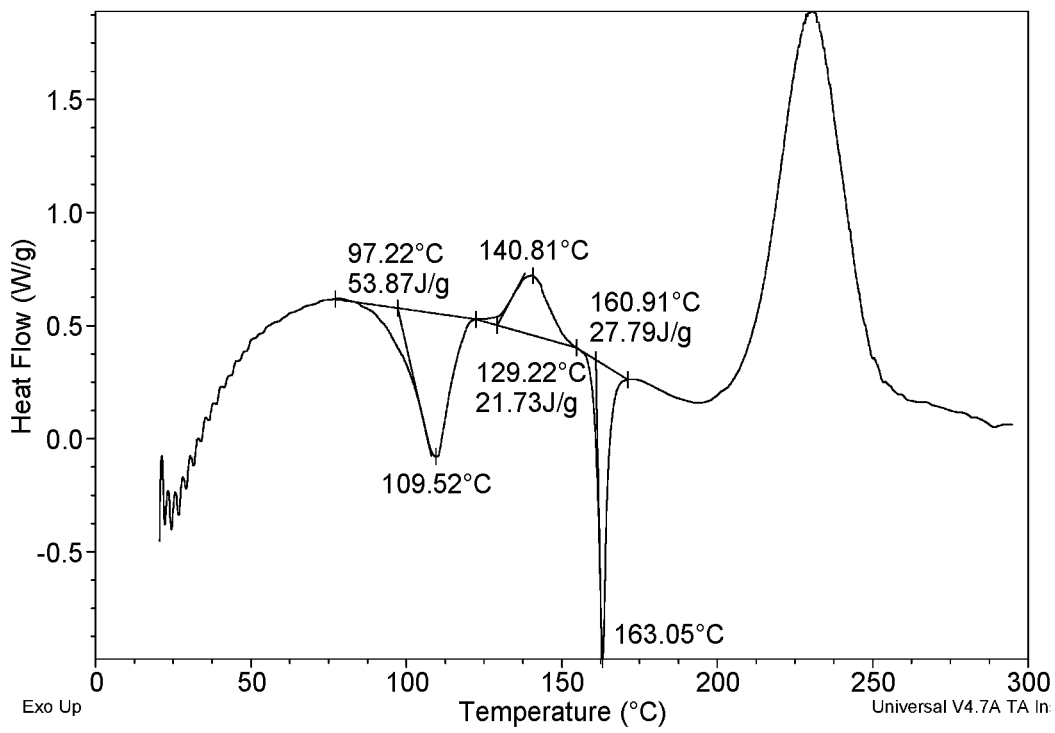
FIG. 8 is a Differential Scanning calorimeter (DSC) curve of Crystal form III of Compound A.
Figure 9:
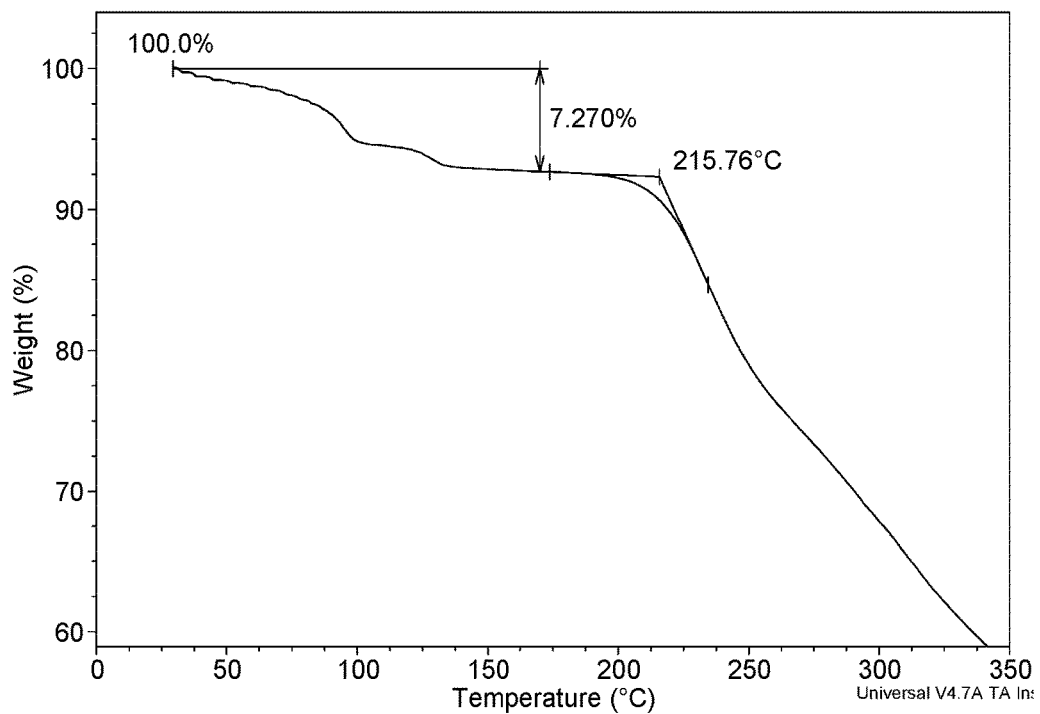
FIG. 9 is a Thermogravimetric Analysis (TGA) curve of Crystal form III of Compound A.

Method 1: At room temperature, Crystal form I of Compound A (50 mg) was dissolved in tetrahydrofuran (5.0 ml), followed by filtration. Methylcyclohexane (5.0 ml) was added dropwise under stirring to precipitate a large amount of white solid, followed by further stirring for 10 min and filtration. The filter cake was vacuum-dried at room temperature to obtain Crystal form III of Compound A, which was characterized by XRD, DSC and TGA as shown in FIGS. 7-9.

EXAMPLE 4

Preparation of Crystal Form IV of Compound A

Figure 10:
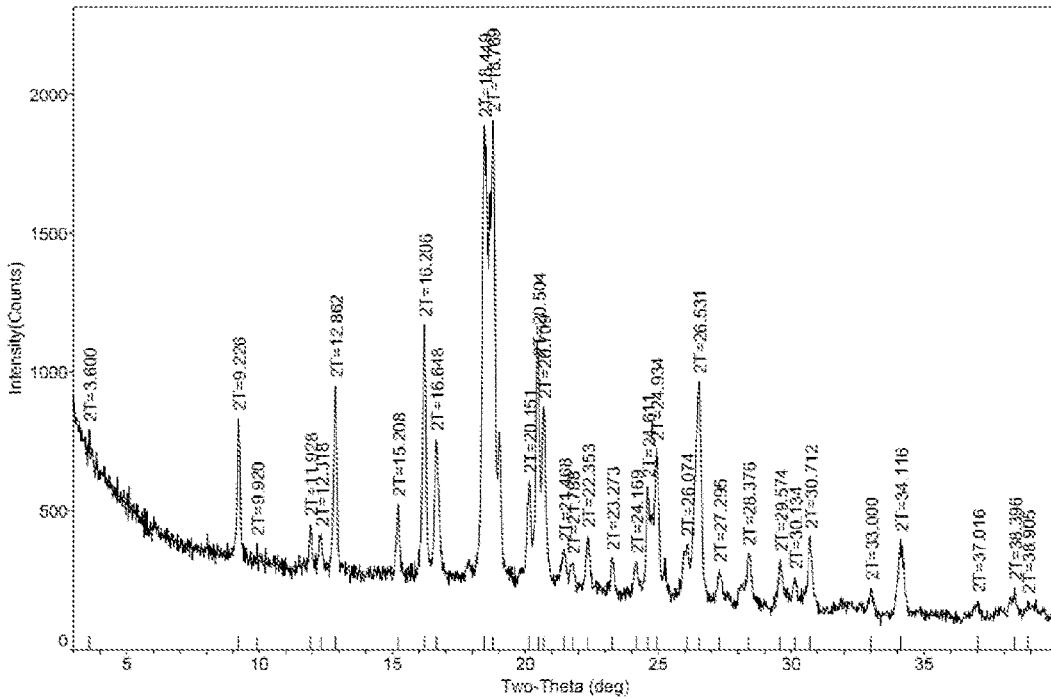
FIG. 10 is an X-ray powder diffraction pattern of Crystal form IV of Compound A, obtained using Cu—Kα radiation.
Figure 11:
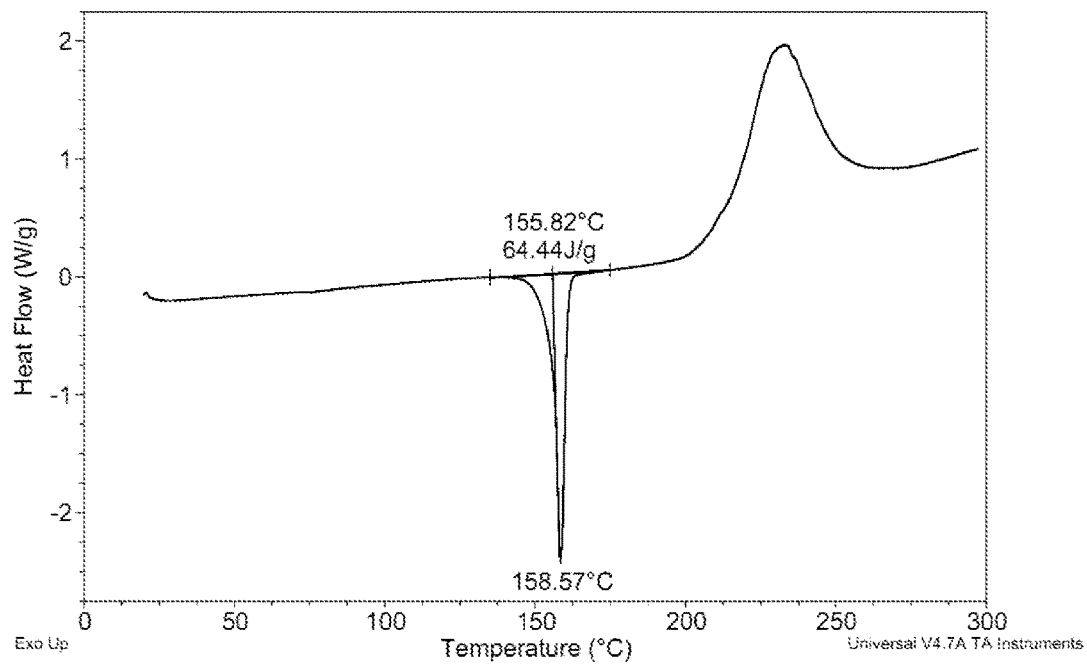
FIG. 11 is a Differential Scanning calorimeter (DSC) curve of Crystal form IV of Compound A.
Figure 12:
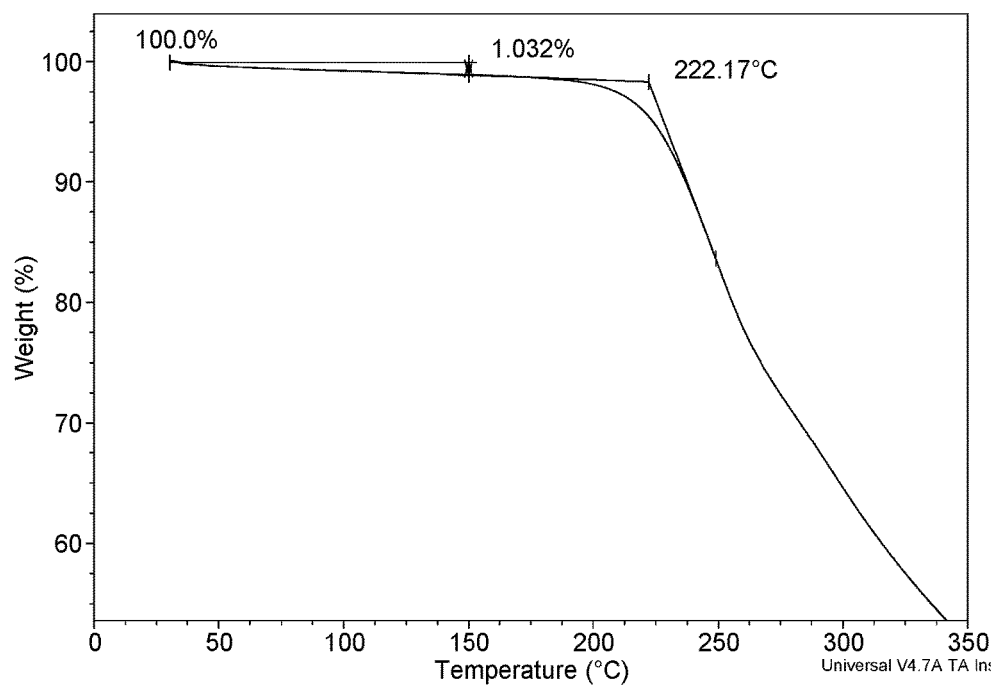
FIG. 12 is a Thermogravimetric Analysis (TGA) curve of Crystal form IV of Compound A.

Method 1: At a temperature not higher than 50° C., 60 g of Crystal form I of Compound A was dissolved in ethyl acetate (480 ml), and n-heptane (960 ml) was added dropwise under stirring. Then the temperature was decreased to room temperature, followed by further stirring for 2 hours and filtration, to obtain a white solid, which was characterized by XRD, DSC and TGA as Crystal form IV of Compound A, as shown in FIGS. 10-12. Method 2: Crystal form I of Compound A (50 mg) was placed in an air dry oven and heated to 140° C. which was held for 5 min, to obtain Crystal form IV of Compound A, which had the same pattern or curves as FIGS. 10-12.

Method 2: Crystal form I of Compound A (10 mg) was added to ethanol (0.5 ml), methyl t-butyl ether (0.5 ml), n-heptane (0.5 ml), water/ethanol (1 ml/1 ml) or water/n-heptane (0.3 ml/0.3 ml), to obtain a suspension, which was allowed to slurry at room temperature for 3 days. Then the resultant slurry suspension was centrifuged to obtain Crystal form IV of Compound A, which had the same pattern or curves as FIGS. 10-12.

Method 3: Crystal form I of Compound A (10 mg) was added to water/ethanol (1.0 ml/0.5 ml) or ethanol/n-heptane (0.5 ml/0.1 ml) to obtain a suspension, which was allowed to slurry at 40° C. for 3 days. The resultant slurry suspension was centrifuged to obtain Crystal form IV of Compound A, which had the same pattern or curves as FIGS. 10-12.

Method 4: At room temperature, Crystal form I of Compound A (10 mg) was dissolved in methanol (0.4 ml), and water (2.0) was added dropwise at stirring until a solid was precipitated, followed by centrifugation to obtain Crystal form IV of Compound A, which had the same pattern or curves as FIGS. 10-12. Following this method, Crystal form IV of Compound A can also be obtained using the good solvent-anti-solvent system of methanol-isopropyl ether (0.4 ml/5.0 ml) and has the same pattern or curves as FIGS. 10-12. Following this method, Crystal form IV of Compound A can also be obtained using the good solvent-anti-solvent system of ethanol-n-heptane (0.4 ml/4.0 ml) at 70° C. and has the same pattern or curves as FIGS. 10-12.

Method 5: Crystal form I of Compound A (10 mg) was placed in a small bottle, and water/ethanol (1.0 ml/0.6 ml) was added at 70° C. to obtain a clear solution, which was directly stirred at room temperature to precipitate a solid, to obtain Crystal form IV of Compound A, which had the same pattern or curves as FIGS. 10-12.

EXAMPLE 5

Stability of Crystal Forms

1. The stability of the crystal forms of Compound A is shown in Table 1.

TABLE 1

Stability of crystal forms of Compound A

| Crystal form before transformation | Transformation condition | Crystal form after transformation |
| --- | --- | --- |
| Crystal form II | Kept dry at room temperature for 14 d | Crystal form II |
| Crystal form III | Kept dry at room temperature for 14 d | Crystal form III |
| Crystal form IV | Kept dry at room temperature for 14 d | Crystal form IV |

Crystal forms II, III and IV of Compound A have good stability.

2. Room temperature competition experiment between Crystal form I and Crystal forms II, III, IV of Compound A, examining the stability of the crystal forms in solvents such as water, ethanol, and water:ethanol (1:1) at room temperature, see Table 2 for details.

TABLE 2

Slurry competition experiments of crystal forms of Compound A

| Crystal form | Experimental condition | XRD results |
| --- | --- | --- |
| Mixed sample of Crystal form I and Crystal forms II, III, IV of Compound A in equal weights | Competing for slurrying for 2 days in water | Crystal form IV |
| | Competing for slurrying for 2 days in ethanol | Crystal form IV |
| | Competing for slurrying for 2 days in water:ethanol (1:1) | Crystal form IV |

From the above crystal slurry competition experiments between crystal forms of Compound A, it can be seen that Crystal form IV is the most stable crystal form at room temperature.

EXAMPLE 6

Enzymatic Screening Experiment of Crystal Form IV of Compound a on Plasma DPP-IV in Dogs Male beagle dogs having similar body weights and ages were grouped (n=3). On the day before the experiment, the beagle dogs were fasted for 8 hours but allowed access to water. Body weights of the animals were measured on the day of experiment. The animals were administered with a capsule of Crystal form IV of Compound A (prepared by direct filling Crystal form IV of Compound A into the capsule shell) at a dose of 10.0 mg/kg based on their body weight. Blood samples were taken right before administration (0 h), and 0.5, 1, 2, 4, 8, 12, 24, 32, 48, 56, 72, 80, 96, 104, 120, 128, 144, 152, 168, 192, 216, and 240 h after administration. At each time point, 1 ml blood was added to an EDTA anticoagulation tube and centrifuged at a low temperature at 2500 rpm for 15 min, and then the plasma was drawn and dispensed into two 1.5-ml EP tubes and stored at −80° C. Animal feed was given one hour after administration. 40 μl plasma was taken from each test sample, and 10 μl H-Ala-Pro-AFC substrate (0.2 mM) was added thereto, followed by reaction for 5 min, in which a substrate-free well was used as the blank. The reaction was read with a microplate reader (Wavelength of excitation=405 nm, Wavelength of emission=535 nM). Inhibition of enzyme activity was calculated according to the following equation:

Inhibition (%)=[1−(Response of compound−Response of blank)/(Response before administration−Response of blank)]*100%.

Figure 13:
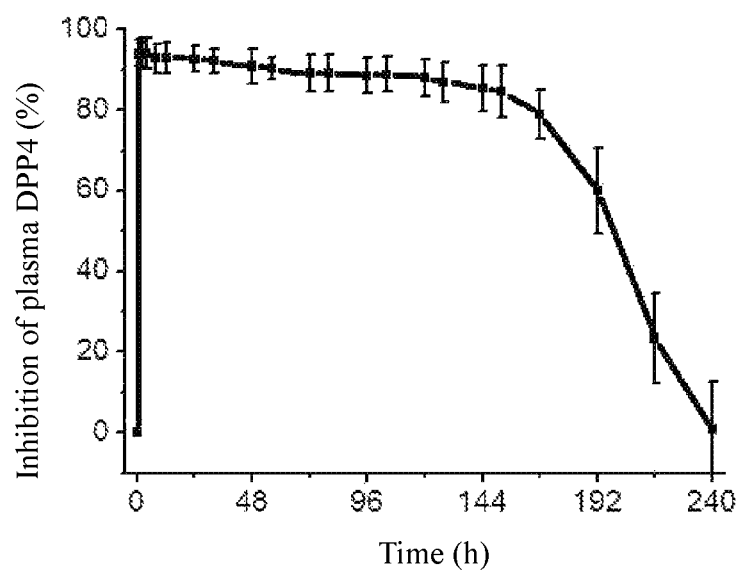
FIG. 13 shows the results of an enzymatic experiment of Crystal form IV of Compound A on dog blood plasma DPP-IV.

The results were plotted with Origin 7.5. The period during which the inhibition of plasma DPP-IV enzymatic activity was 80% was calculated for Crystal form IV of Compound A, and the results are shown in Table 3 and FIG. 13.

Preparation of H-Ala-Pro-AFC substrate: a suitable amount of the substrate was dissolved in DMSO and formulated into a solution at a concentration of 10 mM.

TABLE 3

Results of enzymatic screening experiment on plasma DPP-IV in beagle dogs.

| Test Compound | Duration of Inhibition 80% |
|---|---|
| Crystal form IV of Compound A | 165 h |

EXAMPLE 7

Investigation of Chemical Stability of Crystal Form IV of Compound A

Experimental Conditions

A sample was investigated under the conditions and sampling time points shown in Table 4 below for influencing factors, and the results are shown in Table 5 below.

TABLE 4

Experimental conditions and influencing factors

| Experimental conditions | 40° C. | Light exposure | 92.5% RH | 60° C. |
|---|---|---|---|---|
| Sampling points | 10 d, 60 d | 10 d, 60 d | 10 d, 60 d | 10 d, 60 d |
| Requirement of placement | | Unsealed, open to the air | | |

Experimental Results:

TABLE 5

Experimental results under high temperatures, light exposure and high humidity

| Experimental conditions | | Investigation | | Appearance | Moisture | Purity of Compound A |
|---|---|---|---|---|---|---|
| High temperature | | | 0 d | Off-white powder | 0.19% | 99.67% |
| | Unsealed | 40° C. | 10 d | Light yellow powder | 0.25% | 99.54% |
| | | | 60 d | Light yellow powder | 0.18% | 99.43% |
| | | 60° C. | 10 d | Light yellow powder | 0.36% | 99.48% |
| | | | 60 d | Light yellow powder | 0.15% | 99.15% |
| Light exposure | Unsealed | Light exposure | 10 d | Off-white powder | 0.32% | 99.51% |
| | | | 60 d | Off-white powder | 0.16% | 99.43% |
| High humidity | Unsealed | High humidity | 10 d | Light yellow powder | 0.27% | 99.57% |
| | | | 60 d | Light yellow powder | 0.20% | 99.28% |

Conclusion: At high temperatures, light exposure or high humidity, the purity of Compound A was substantially unchanged at day 10 or day 60, showing excellent chemical stability.

The invention claimed is:
1. Crystal form IV of the compound of formula (I):

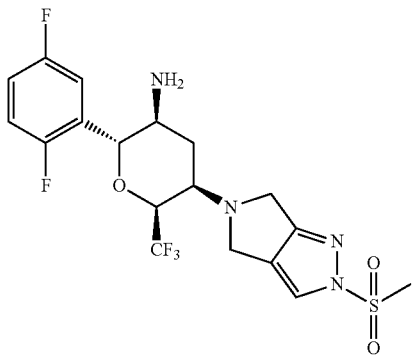

(I)

wherein the X-ray powder diffraction pattern of Crystal form IV measured using Cu—Kα radiation contains characteristic diffraction peaks present at 2θ positions of 9.2°±0.2°, 12.8°±0.2°, 16.2°±0.2°, 18.4°±0.2°, 20.5°±0.2° and 26.5°±0.2°.

2. The crystal form according to claim 1, wherein the X-ray powder diffraction pattern of Crystal form IV measured using Cu—Kα radiation contains additional characteristic diffraction peaks present at 2θ positions of 11.9°±0.2°, 12.3°±0.2°, 15.2°±0.2°, 16.6°±0.2°, 18.7°±0.2° and 24.9°±0.2°.

3. The crystal form according to claim 2, wherein the X-ray powder diffraction pattern of Crystal form IV measured using Cu—Kα radiation contains additional characteristic diffraction peaks present at 2θ positions of 20.1°±0.2°, 20.7°±0.2°, 21.4°±0.2°, 22.3°±0.2°, 23.2°±0.2° and 24.6°±0.2°.

4. The crystal form according to claim 3, wherein the X-ray powder diffraction pattern of Crystal form IV is substantially as shown in FIG. 10.

5. The crystal form according to claim 1, wherein a Differential Scanning Calorimeter curve of the crystal is as shown in FIG. 11, or a Thermogravimetric Analysis curve of the crystal is as shown in FIG. 12.

6. A pharmaceutical composition comprising a therapeutically effective amount of the crystal form according to claim 1, and a pharmaceutically acceptable carrier or excipient.

7. A method for treating a metabolic disease, comprising administering the crystal form according to claim 1.

8. A method for preparing Crystal form IV of the compound of formula (I), comprising subjecting the amorphous form of the compound of formula (I) or any crystal form of the compound of formula (I) to recrystallization or slurrying, wherein the solvent for the recrystallization or slurrying is selected from one of, or a mixed solvent of two or more of, ester solvents, ether solvents, alkane solvents, and water.

9. The method according to claim 8, wherein the solvent for the recrystallization or slurrying is selected from one of, or a mixed solvent of two or more of, ethyl acetate, isopropyl ether, methyl t-butyl ether, n-heptane, methanol, ethanol, and water.

10. The method according to claim 8, wherein the temperature for the recrystallization or slurrying is 10° C. to 80° C.

11. The method according to claim 8, wherein the solvent for the recrystallization or slurrying is a mixed solvent of ethyl acetate and n-heptane.

12. A method for preparing Crystal form IV of the compound of formula (I), comprising treating the amorphous form of the compound of formula (I) or any crystal form of the compound of formula (I) at a temperature of 100° C. or higher.

13. The method according to claim 12, wherein the temperature is 140° C.

14. The method according to claim 7, wherein the metabolic disease is diabetes, diabetic retinopathy, diabetic neuropathy, or diabetic nephropathy.

15. The method according to claim 7, wherein the metabolic disease is type II diabetes.

16. The method according to claim 10, wherein the temperature for the recrystallization or slurrying is 10° C. to 50° C.

17. The method according to claim 11, wherein the volume ratio of ethyl acetate and n-heptane is 1:1 to 1:3.

18. The method according to claim 11, wherein the volume ratio of ethyl acetate and n-heptane is 1:2.

* * * * *